US012272268B2

(12) United States Patent
Gao et al.

(10) Patent No.: US 12,272,268 B2
(45) Date of Patent: Apr. 8, 2025

(54) IMMERSIVE ANKLE REHABILITATION TRAINING METHOD AND ELECTRONIC APPARATUS BASED ON UPPER LIMB MOTION SIGNALS

(71) Applicant: Beihang University, Beijing (CN)

(72) Inventors: Yang Gao, Beijing (CN); Yanqing Xiao, Beijing (CN); Jia Zheng, Beijing (CN); Aimin Hao, Beijing (CN); Hongming Bai, Beijing (CN)

(73) Assignee: Beihang University, Beijing (CN)

( * ) Notice: Subject to any disclaimer, the term of this patent is extended or adjusted under 35 U.S.C. 154(b) by 0 days.

(21) Appl. No.: 18/601,573

(22) Filed: Mar. 11, 2024

(65) Prior Publication Data

US 2024/0312361 A1    Sep. 19, 2024

(30) Foreign Application Priority Data

Mar. 13, 2023  (CN) .......................... 202310250089.6

(51) Int. Cl.
   *G09B 9/00*    (2006.01)
   *A61B 5/00*    (2006.01)
   *A61B 5/389*   (2021.01)

(52) U.S. Cl.
   CPC ................ *G09B 9/00* (2013.01); *A61B 5/389* (2021.01); *A61B 5/681* (2013.01); *A61B 5/744* (2013.01)

(58) Field of Classification Search
   CPC ...... G09B 9/00; G09B 19/00; G09B 19/0015; G09B 19/003; G09B 19/0038; A61B 5/389; A61B 5/681; A61B 5/744
   See application file for complete search history.

(56) References Cited

U.S. PATENT DOCUMENTS

| | | | |
|---|---|---|---|
| 2021/0086024 A1* | 3/2021 | McCarthy | G16H 50/30 |
| 2024/0148301 A1* | 5/2024 | Chang | A61B 5/6831 |
| 2024/0399207 A1* | 12/2024 | Hanein | A61B 5/1123 |

* cited by examiner

*Primary Examiner* — Timothy A Musselman

(57) ABSTRACT

This disclosure relates to an immersive ankle rehabilitation training method and electronic apparatus based on upper limb motion signals. The innovation of this technology lies in that: firstly, this disclosure proposes a hybrid model of Regression LSTM corrected by a sliding window based voting algorithm, which predicts the changing angle of the user's wrist joint through wearable EMG sensors; secondly, this disclosure designs and develops two different VR training scenes for users of dorsiflexion and plantar flexion of foot; during the training, users wear VR headwear displays and EMG monitoring devices, to continuously perform wrist dorsiflexion or wrist palm flexion movements, predict the change in wrist joint angles in real-time through forearm sEMG signals, and map it to the contralateral ankle of the avatar in the virtual scene for rotation.

20 Claims, 7 Drawing Sheets

IMMERSIVE ANKLE REHABILITATION TRAINING METHOD AND ELECTRONIC APPARATUS BASED ON UPPER LIMB MOTION SIGNALS

CROSS-REFERENCE TO RELATED APPLICATION

This application claims priority from the Chinese patent application 2023102500896 filed Mar. 13, 2023, the content of which is incorporated herein in the entirety by reference.

TECHNICAL FIELD

This disclosure relates to the technical field of virtual reality application, and specifically to a motor function rehabilitation training and evaluation technology based on virtual reality technology.

BACKGROUND

Under the influence of aging population and many uncontrollable comprehensive factors, the number of patients with limb motor dysfunction is increasing year by year. Based on the plasticity of mirror neurons in the brain, adopting timely and effective task oriented autonomous rehabilitation training stimulation for early acute or subacute hemiplegia patients, and in combination with modern rehabilitation methods such as action observation, motor imagination, and imitation learning, can promote the repair and reorganization of brain motor tissue and compensate for the missing functions of damaged nerve cells, thereby achieving the goal of rehabilitation. Compared to traditional treatment plans, the rehabilitation mode of VR (Virtual Reality) technology can provide patients with a stronger sense of immersion in the field and elevate the central sensory stimulation level of patients in multiple aspects, with such characteristics as increasing patients' enthusiasm for the treatment, enhancing their cognitive ability to the ambiance, and improving the friendliness of the training environment. The sEMG (surface electromyography) signal, as a bioelectric feedback signal in the human body, can accurately reflect information of different muscles in terms of activity timing, activity intensity, fatigue status, and etc., and has been widely used in multiple fields of rehabilitation medicine.

In order to solve the problem of the early clinical hemiplegic patients' limited autonomous movement, the introduction of modern motor imagination rehabilitation mode and the exploration of the influence of sEMG signal active intention collaborated with excitation and stimulation on motor imagination performance and kinesthetic illusion in VR scenes have important research significance and application value.

The technical problem addressed in this disclosure is: to propose using the sEMG signal of the user's contralateral uninjured wrist joint movement as the starting signal for virtual ankle movement, controlling virtual lower limb movement in VR scenes, and conducting rehabilitation training for lower limb motor function, thereby improving the user's kinesthetic illusion and sense of physical belonging, and enhancing the effectiveness of rehabilitation training.

SUMMARY

The content of this disclosure is to briefly introduce concepts, which will be described in detail in the section of detailed description of the disclosure later. The content of this disclosure is not intended to identify key or necessary features of the claimed technical solution, nor is it intended to limit the scope of the claimed technical solution.

Some embodiments of this disclosure involve a virtual and real collaborative interaction method based on upper limb motion signal feedback to solve one or more of the technical problems mentioned in the background of the disclosure above.

This disclosure relates to a virtual and real collaborative interaction method based on upper limb motion signal feedback. This technology comprises: Firstly, this disclosure proposes a hybrid model of Regression LSTM corrected by a sliding window based voting algorithm, which predicts the changing angle of the user's wrist joint through wearable EMG sensors; Secondly, this disclosure designs and develops two different VR rehabilitation training scenes for users of dorsiflexion and plantar flexion of foot; During motor rehabilitation training, users wear VR headwear displays and EMG monitoring devices (such as EMG monitoring bracelets) to continuously perform wrist dorsiflexion or wrist palm flexion movements. The system obtains skin sEMG signals from 8 channels on the forearm in real-time, predicts the current angle of changes in the wrist joint, maps them to the ankle of the person on the contralateral side of the arm in the virtual scene and rotates, thereby realizing collaborative stimulation of virtual and real limb integration, and enhancing the rehabilitation training effect on lower limb motor function.

The principle of this disclosure lies in the introduction of VR technology, which innovates the monitoring of hand movements through contralateral forearm sEMG signals integrating the virtual with the real, controls the mode of virtual leg movement, changes the degree of contraction and relaxation of related muscle groups, regulates subjective consciousness, being able to enhance the users' motor imagination vividness, kinesthetic illusion, and sense of physical belonging, thereby achieving the goal of promoting motor function rehabilitation training.

The principle of using contralateral hand sEMG signals to control the virtual foot movement on the affected side is that hemiplegic patients who require lower limb motor function training often lose both lower and upper limb motor functions on the same side, making it difficult to use the same side hand movement to control the virtual leg. The mode of controlling virtual leg movements by the contralateral uninjured hand sEMG can maximize coverage for post-stroke hemiplegic users.

A data-driven hybrid network model, Regression LSTM, is proposed for the recognition of continuous EMG signals, and a filtering vote correction algorithm based on a sliding window is designed in regard to the sEMG signals' characteristics of being weak and susceptible to interference. This ensures correct recognition of continuous actions while maintaining fairly high time efficiency, with higher accuracy and robustness compared to existing methods. A virtual and real collaborative feedback rehabilitation training mode based on continuous sEMG signals is designed and implemented. Two different rehabilitation training scenes (treasure box pulling and football pushing games) are designed respectively for patients with dorsiflexion and plantar flexion of foot, which can enhance the users' motor imagination vividness, kinesthetic illusion, and sense of physical belonging, and reduce the effort of motor imagination.

BRIEF DESCRIPTION OF THE DRAWINGS

The above and other features, advantages, and aspects of the embodiments of this disclosure will become more apparent in conjunction with the accompanying drawings and with reference to the following specific implementations. Throughout the drawings, the same or similar reference signs indicate the same or similar elements. It should be understood that the drawings are schematic, and the components and elements are not necessarily drawn to scale.

DETAILED DESCRIPTION

Figure 1:
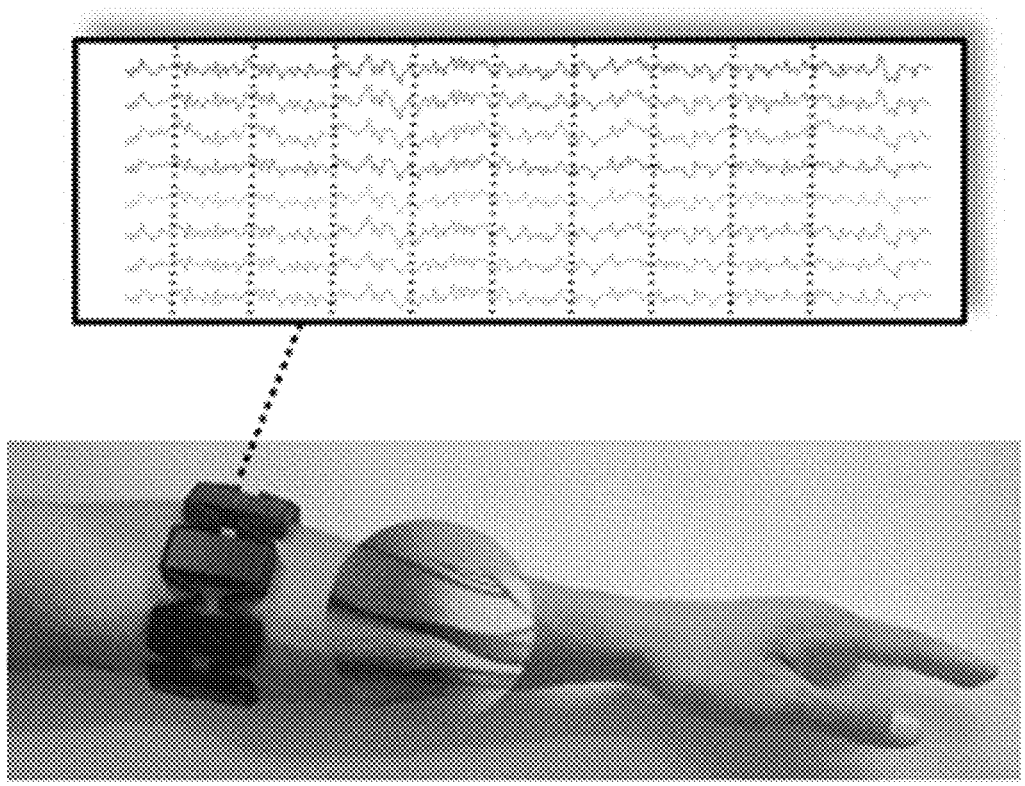
FIG. 1 is a schematic diagram of sEMG signal acquisition for an immersive ankle rehabilitation training method based on upper limb motion signals according to this disclosure.

Hereinafter, the embodiments of this disclosure will be described in more detail with reference to the accompanying drawings. Although certain embodiments of this disclosure are shown in the drawings, it should be understood that this disclosure may be implemented in various forms, and shall not be construed as being limited to the embodiments set forth herein. On the contrary, these embodiments are provided for a more thorough and complete understanding of this disclosure. It should be understood that the drawings and embodiments of this disclosure are used only for illustrative purposes, not to limit the protection scope of this disclosure.

Besides, it should be noted that, for ease of description, only the portions related to the relevant disclosure are shown in the drawings. In the case of no conflict, the embodiments in this disclosure and the features in the embodiments may be combined with each other.

It should be noted that such adjuncts as "one" and "more" mentioned in this disclosure are illustrative, not restrictive, and those skilled in the art should understand that, unless the context clearly indicates otherwise, they should be understood as "one or more".

In this disclosure, since the target users are mainly patients who need rehabilitation training, the term 'patient' has the same meaning as the user in the following text.

This disclosure will be described in detail below with reference to the accompanying drawings and in conjunction with embodiments.

The immersive ankle rehabilitation training method based on upper limb motion signals comprises the following steps:

Step 1, initializing a hybrid network model, Regression LSTM model, and in combination with a filtering vote correction algorithm based on a sliding window, to perform recognition of sEMG signals, wherein, the Regression LSTM model is obtained by weighting the machine learning based regression model Regression and the deep learning based long and short term memory network LSTM, and the weighting is based on the determination coefficient R2 score of the training sample.

Step 2, entering a virtual and real collaborative interactive feedback rehabilitation training system based on continuous sEMG signals, wherein the training system comprises two virtual training scenes, namely a treasure box pulling virtual training scene for foot dorsiflexion training and a football pushing virtual training scene for foot plantar flexion training, wherein, each of two virtual training scenes included in the training system has a virtual avatar, the two feet of the virtual avatar are placed flat and vertically on a yoga mat, and a floor texture is added to the ground, the front is a marble texture, there are buttons in the upper left and upper right of the two scenes respectively to control whether the legs are to be displayed, for upper and lower limb alignment and direction coordination training. The virtual training scene included in the training system has "Left Move" or "Right Move" buttons; to display the leg on the current side, click on the "Left Move" or the "Right Move" button, the prompt on the button at the time will change to "Left Stop" or "Right Stop", and the virtual leg, rate control bar, and horizontal and vertical scrolling progress bars in two different dimensional directions will appear simultaneously, wherein, the rate control bar is used to control the rate of change of the scrolling progress bar, the scrolling progress bar continuously changes at a constant speed in both horizontal and vertical directions, with the main purpose of providing users with a reference rate of wrist dorsiflexion and wrist palm flexion movements, so that they can follow the wrist joint movement.

Wherein, the filtering vote correction algorithm based on a sliding window comprises:

The first step is introducing a sliding window, wherein, the number of small windows selected by the sliding window is odd so as to calculate symmetry, and each small window is assigned a weight value.

The second step is filling the entire sliding window up with an odd number of original sEMG signal values.

The third step is starting from half the sliding window, calculating this value by multiplying the weight of the entire sliding window by the odd number of original sEMG signal values to obtain a correction value, the calculation formula is as follows:

$$ProData_i = \sum\nolimits_{j=-\lfloor \frac{w}{2} \rfloor}^{\lfloor \frac{w}{2}+1 \rfloor} W_{j+\lfloor \frac{w}{2} \rfloor} \times RawData_{i+j}.$$

Wherein, i represents the serial number, $ProData_i$ represents the $i^{th}$ data after sliding window correction, $\Sigma$ represents a summation symbol, w represents the size of the sliding window, j represents the serial number, W represents the weight value of the sliding window, and represents the weight value of the $j^{th}$ sliding window, $RawData_{i+j}$ represents the $(i+j)^{th}$ data among the odd number of original sEMG signal values.

Based on the sliding window voting correction algorithm, iterative calculation is carried out sequentially until the $$\left(n - \left\lfloor \frac{w}{2} \right\rfloor \right)^{th}$$

data, then the $$\left\lfloor \frac{w}{2} + 1 \right\rfloor^{th}$$

original sEMG signal values are filled in, wherein n represents the maximum value of i, and compared to existing sliding window algorithms, an additional original sEMG signal value is filled in to overlay adjacent windows to ensure a smooth transition of sEMG continuous signals.

The fifth step is performing boundary correction on the processed data ProData: using the following formula $$\begin{cases} \text{Corr}\,Fac = \dfrac{\text{Max} - (\text{Test Set Label}_i) - \text{Min}\,(\text{Test Set Label}_i)}{\text{Max}\,(Pro\,\text{Data}_i) - \text{Min}\,(Pro\,\text{Data}_i)}, i = 0, \ldots, n-1 \\ \text{Corr Data}_i = (Pro\,\text{Data}_i - 0.5) \times \text{Corr}\,Fac + 0.5 \end{cases}$$

Wherein, CorrFac represents the boundary correction factor, Max( ) represents finding the maximum value, i represents the serial number, $TestSetLabel_i$ represents the $i^{th}$ test set label value, Min( ) represents finding the minimum value, $ProData_i$ represents the $i^{th}$ data after sliding window correction, and n represents the maximum value of i, and $CorrData_i$ represents the final result value after boundary correction.

Step 3, collecting 8 channels of forearm sEMG signals through an EMG bracelet to monitor hand movement, and controlling the contralateral virtual lower limb displayed on the VR headwear display for rehabilitation training, wherein the EMG monitoring bracelet is worn on the user's forearm, the VR headwear display is worn on the user's head, and the user sits upright in a chair. In the end, receiving the Visual Analog Scale (VAS), Likert Scale (LS), Simulator Sickness Questionnaire (SSQ), Intrinsic Motivation Inventory (IMI), Task Load Index (RawTLX), Positive And Negative Affect Scale (I-PANAS-SF), System Usability Scale (SUS), and User Experience Questionnaire (UEQ) filled out by the user after completing rehabilitation training to assist in evaluating the rehabilitation effect.

Wherein, the controlling the contralateral virtual lower limb displayed on the VR headwear display for rehabilitation training comprises:

The first step is using a contralateral wrist sEMG signal of the trained lower limb as a start and control signal for rehabilitation training.

The second step is collecting the sEMG signal changes of the user's forearm, and mapping continuous actions to the avatar's ankle in the virtual scene to perform the same degree of rotation of the foot dorsiflexion/plantar flexion, wherein, the user needs to wear a VR headwear display and an EMG monitoring bracelet to observe the virtual avatar's view of the scene from a first person perspective, the contralateral wrist of the virtual foot continuously performs wrist dorsiflexion/palm flexion movements.

Based on continuous sEMG bioelectric signals, the corresponding wrist joint changes are identified, and the recognition results are mapped to the ankle of the virtual avatar in the VR scene for collaborative movement, establishing an interactive feedback experience of virtual and real collaboration. Active stimulation awakens the patient's originally blurred motion memory, enhances their own limb perception ability, and replaces indirect perception with direct perception in terms of internal information, thereby achieving the goal of rehabilitation. For this purpose, it is first necessary to synchronously collect the sEMG signal of the forearm in real-time when the user makes corresponding actions, and identify and analyze the corresponding continuous wrist joint rotation angle.

1. Acquisition and Preprocessing of sEMG Signals

The core data of this disclosure comes from an EMG collection device. After considering such factors as cost-effectiveness, convenient use at home, and comfortable wearing, the Myo bracelet developed by Thalic Labs Canada in 2013 is used as an EMG collection device for further explanation. It should be noted that the above technology of this disclosure is not limited to the use of Myo bracelets, but can be performed by any device capable of collecting sEMG signals. As shown in FIG. 1, eight sEMG sensors are used to collect sEMG signals and inertial sensor data, and the softdog is transmitted through Bluetooth to communicate with other devices.

Because sEMG signals are unstable and weak bioelectrical signals susceptible to environmental interference, the actually collected sEMG signals are often mixed with a large amount of noise and motion artifacts, resulting in a low signal-to-noise ratio. Therefore, the quality of the extraction and preprocessing of sEMG signals in the early stage is the key that directly affects the accuracy of subsequent wrist joint motion recognition and control. At the same time, the EMG bracelet being worn in what position and scene has the best effect and highest accuracy for recognition of sEMG signals also require relevant experimental verification.

To better improve the accuracy of continuous wrist movement recognition, it is necessary to fully understand the distribution of forearm muscle groups and the force generating muscle groups mapped by wrist dorsiflexion and wrist palm flexion movements. The muscle groups of the human forearm overlap layer by layer, with the anterior side containing the brachioradialis muscle, the radial wrist flexor muscle, the palmaris longus muscle, and the ulnar flexor muscle, and the posterior side containing the ulnar wrist flexor muscle, the ulnar wrist extensor muscle, the radial wrist long extensor muscle, the radial wrist short extensor muscle, the little finger extensor muscle, and the digital extensor muscle. The volume of the muscle group tissue is correlated with the intensity of the sEMG signal. In order to significantly improve the recognition effect of the sEMG signal, it is necessary to place EMG collection patches in areas with larger muscle groups and less interference from adjacent muscle groups. Small amplitude continuous movements such as bending/stretching of the wrist joint and displacement of the radial and ulnar sides mostly involve only shallow muscle groups, while large amplitude movements such as inward and outward supinations involve deep muscle groups. The sEMG signals of shallow muscle groups are easier to detect and collect due to their proximity to the skin surface, while the sEMG signals of deep muscle groups are located deep inside so are difficult to detect and determine the orientation of electrodes.

The continuous wrist joint movements of this disclosure (wrist dorsiflexion/wrist palm flexion) are mainly small amplitude movements, and the Myo bracelet is selected to be worn near the center of the radial extensor carpi longus and radial extensor carpi brevis. The sEMG signal data is transmitted between the Myo bracelet and the computer in a multi-threaded manner to accelerate transmission.

After determining the continuous movement of the wrist joint and the position of the bracelet, the sEMG signal is extracted and preprocessed accordingly. The specific processing method comprises sequentially performing signal differential amplification, common mode suppression, high and low pass filtering, power frequency filtering, and wavelet analysis on sEMG signals to obtain clearer signals. The above processing sequence is a special design of this disclosure for obtaining clear signals.

After obtaining clear preprocessed sEMG signals, event segmentation is required for each EMG activation motor segment, i.e., to determine the angle of change of continuous wrist movements. Monitoring it involves separating the wrist joint activity data from the resting data. Because sEMG signals are a type of one-dimensional timing signals, most algorithms for gesture recognition are based on the entire signal segment and cannot be applied to real-time continuous systems. At the same time, the sEMG signal corresponding to a single sampling point cannot be directly used as an effective input for pattern recognition due to its randomness. It requires continuous accumulation of time to carry out action recognition from the regularity of signal changes over time, then apply the recognition results to real-time control.

2. Training Sample Collection

In this disclosure, the patient ceaselessly performs continuous wrist joint gesture movements (such as wrist dorsiflexion/wrist palm flexion) in an immersive virtual feedback environment by regulating the motor nerve center according to the specific condition of illness, and adjusts the contraction and relaxation intensity of corresponding muscle groups. The system will map sEMG signal feedback to the ankle of the avatar in the virtual scene to make the same movement (such as foot dorsiflexion/foot plantar flexion). The patient continuously attempts and trains the three advanced processes of rehabilitation like movement observation, motor imagination and imitation learning, involving the imagination of one's own ankle making corresponding movements, thereby gradually learning to regulate subjective consciousness, change perception of internal information, achieve interactive and active virtual feedback of lower limb rehabilitation stimulation training, promote motor learning, provide action memory, and reduce motor cortex atrophy caused by damaged limb braking, and in the end, achieving autonomous regulation of this physiological process even without the guidance and feedback assistance of EMG bracelets and VR technology.

In this process, identifying the continuous sEMG signals of the forearm when the patient makes wrist dorsiflexion and wrist palm flexion movements, identifying and analyzing the corresponding continuous action gestures, and further transforming them into actual corresponding floating point variable values (such as rotation angle), is the key to completing this research task. To collect the samples required for subsequent model training, a corresponding VR debugging and collection virtual scene is constructed. In this scene, there is a virtual avatar, and the ankle motion logic of the avatar is set to perform a fixed rate periodic reciprocating motion of foot dorsiflexion/plantar flexion every four seconds (which can be modified through the rate control bar). The user wears an HTC Vive head mounted display and a Myo EMG bracelet, and the real wrist needs to follow the ankle in the virtual scene to perform synchronous wrist dorsiflexion/wrist palm flexion movements at the same rate. The movements can also be synchronized based on the progress bars of both vertical and horizontal dimensions.

During this process, the system will record the 8 channels of sEMG signals of the Myo bracelet, the amplitude value of virtual ankle rotation (normalized), and the timestamp of the running system. Considering that prolonged wrist dorsiflexion/wrist palm flexion movements may lead to muscle fatigue that results in significant deviation of sEMG signal recognition results from actual results, the duration of each sEMG signal acquisition is 1 minute, and after the end of each acquisition, the user relaxes for 10 minutes before proceeding to the next acquisition.

Figure 2:
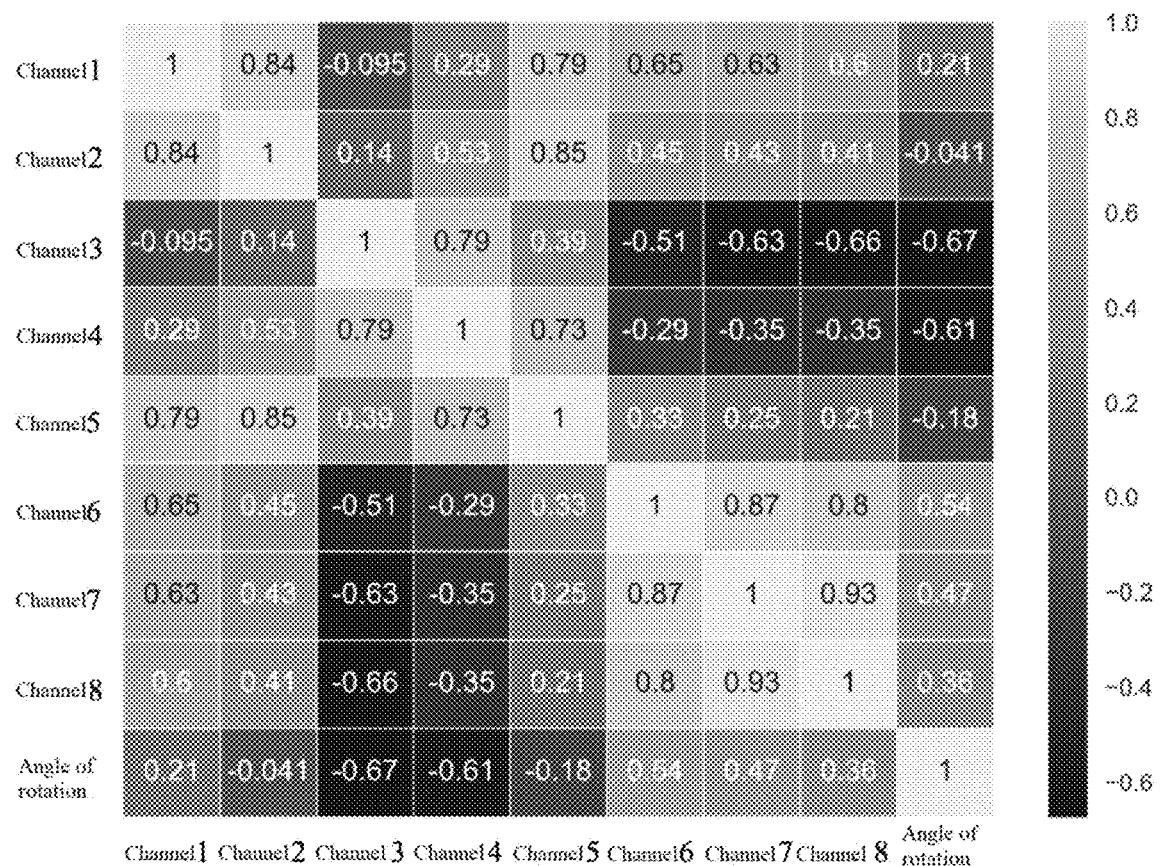
FIG. 2 is a thermal diagram of the correlation between each channel of sEMG signals and virtual ankle rotation amplitude values of an immersive ankle rehabilitation training method based on upper limb motion signals according to this disclosure.

In the end, a total of 5 sets of data were collected in the experiment, comprising three sets as training sets (8931 samples), 1 set as testing sets (2977 samples), and 1 set as validation sets (2978 samples). FIG. 2 shows the correlation between the sEMG signal of each channel and the virtual ankle rotation amplitude value. It can be seen that the correlation between the ankle rotation amplitude value and each channel is in order of 3, 4, 6, 7, 8, 1, 5, 2.

3. A Data Driven Hybrid Network Model

The existing continuous joint recognition algorithms based on sEMG signals are difficult to reliably and accurately distinguish different angle change values. In order to map the identified wrist joint motion sEMG signal more accurately and quickly to the virtual ankle, this disclosure innovatively proposes a data-driven robust hybrid network Regression LSTM model, which assigns different weights to the machine learning based regression model and the deep learning based LSTM model to increase system robustness, striving to balance accuracy and real-time performance without affecting the recognition effect. Besides, a vote filtering correction algorithm based on a sliding window is designed in regard to the sEMG signals' characteristics of being weak and susceptible to interference, and experimental results are compared and verified with the original separate machine learning model and deep learning model.

The basis for mixed weights is the accuracy measurement of the network model, using $R^2$ score as the accurate performance measurement standard, whose error benchmark chooses a mean to determine whether the prediction result error is greater or less than the mean benchmark error.

The specific calculation formula is as follows:

(1) Calculate the Explained Sum of Squares (ESS), which refers to the error between the estimated value and the average value, reflecting the sum of squared deviations in the degree of correlation between the independent variable and the dependent variable.

$$ESS = \sum_{i=1}^{n}(\hat{y}_i - \bar{y})^2.$$

Wherein, ESS represents the calculation of the explained sum of squares, i represents the serial number, $\Sigma$ represents a summation symbol, n represents the maximum value of i, $\hat{y}_i$ represents the estimated value of the sample, $\bar{y}$ represents the average value of the sample.

(2) Calculate the Residual Sum of Squares (RSS), which refers to the error between the estimated value and the true value, reflecting the overall fit of the model.

$$RSS = \sum_{i=1}^{n}(y_i - \hat{y}_i)^2.$$

Wherein, RSS represents the calculation of the residual sum of squares, $y_i$ represents the true value of the $i^{th}$ sample.

(3) Calculate the Total Sum of Squares (TSS), which refers to the error between the average value and the true value, reflecting the degree of deviation from mathematical expectations $$TSS = ESS + RSS = \sum_{i=1}^{n}(y_i - \bar{y})^2.$$

Wherein, TSS represents the calculation of the total sum of squares.

(4) Calculate the $R^2$ score, reflecting the proportion of all variations in the dependent variable that can be explained by the independent variable through a regression relationship.

$$R^2 = 1 - \frac{RSS}{TSS} = 1 - \frac{\sum_{i=1}^{n}(y_i - \hat{y}_i)^2}{\sum_{i=1}^{n}(y_i - \bar{y})^2}.$$

Wherein, $R^2$ represents the $R^2$ score.

When the $R^2$ score is closer to 1, the predicted effect of the sample is better. Conversely, when the $R^2$ score is closer to 0, the predicted effect of the sample is worse. When the $R^2$ score is equal to 1, it indicates that the predicted value in the sample is completely equal to the true value without any error, indicating that the independent variable in the regression model has a better interpretation of the dependent variable. When the $R^2$ score is equal to 0, the numerator and denominator meet, and each predicted value of the sample is equal to the mean. When the $R^2$ score is negative (i.e. the mean is less than the variance), it indicates that the model has weak recognition ability and cannot meet the prediction requirements.

The EMG wrist joint motion recognition method based on traditional machine learning strongly relies on extracting corresponding EMG signal features, and the quality of feature selection often directly determines the final performance of continuous motion recognition. Its recognition speed is fast, but accuracy may decrease with the increase of overall motion complexity. The EMG wrist joint motion recognition method based on deep learning can automatically learn features of different abstract levels directly from a large number of input samples through representation learning, which may greatly avoid the complex and tedious process of signal feature extraction and optimization, thus achieving end-to-end pattern recognition. Although its recognition accuracy is high, there is some uncertainty due to the black box nature.

In order to further enhance the robustness of the overall model, different proportions of weight were assigned to the optimal integrated machine learning model ($W_M$=0.2112) and the optimal integrated deep learning model ($W_D$=0.7888) through grid search, forming a data-driven robust hybrid network Regression-LSTM model, which further improves recognition accuracy within an acceptable range of time delays. After verification by the test set, the $R^2$ score of the final hybrid network Regression LSTM model is 0.8486, the predicted time is 1054.7591 ms, and its $R^2$ score is currently the highest among all models.

4. Voting Correction Algorithm Based on Sliding Window

Due to the fact that sEMG signals are a type of unstable and easily interfered bioelectric signals, especially in the recognition of continuous changes in skeletal joint movements, actual tests have shown that the wrist inevitably produces some small tremors during wrist dorsiflexion and wrist palm flexion movements, resulting in small tremors when the avatar's ankle rotates in the process of mapping sEMG signal recognition analysis results to the virtual scene. Therefore, this article designs and implements a voting correction algorithm (VCA) based on a sliding window to solve this problem.

This disclosure introduces a sliding window. In order to facilitate the calculation of symmetry, the number of selected windows is odd, and each small window is assigned a weight value. Taking window size 7 as an example, first fill the entire sliding window up with original data values (initially 7 sEMG signal values), then start from half the sliding window (index 3), calculate this value by multiplying the weight of the entire sliding window by the original data to obtain a correction value, namely:

$$Pro\,Data_i = \sum_{j=-\lfloor\frac{w}{2}\rfloor}^{\lfloor\frac{w}{2}+1\rfloor} W_{j+\lfloor\frac{w}{2}\rfloor} \times Raw\,Data_{i+j}.$$

Wherein, i represents the serial number, $ProData_i$ represents the $i^{th}$ data after sliding window correction, $\Sigma$ represents a summation symbol, w represents the size of the sliding window, j represents the serial number, W represents the weight value of the sliding window, and represents the weight value of the $j^{th}$ sliding window, $RawData_{i+j}$ represents the $(i+j)^{th}$ data among the odd number of original sEMG signal values.

Based on the sliding window voting correction algorithm, iterative calculation is carried out sequentially until the $$\left(n - \left\lfloor\frac{w}{2}\right\rfloor\right)^{th}$$

data, then the $$\left\lfloor\frac{w}{2} + 1\right\rfloor^{th}$$

original sEMG signal values are filled in, wherein n represents the maximum value of i, and compared to existing sliding window algorithms, an additional original sEMG signal value is filled in to overlay adjacent windows to ensure a smooth transition of sEMG continuous signals.

Due to the use of a sliding window based voting correction algorithm, when predicting the results of the analysis amplitude region, its range will be correspondingly reduced, resulting in the inability to balance the calculation of boundary values. In other words, values near 0 or 1 will shrink towards the middle due to the weight assignment of the sliding window, thereby affecting the range ability.

Perform boundary correction to the processed data $ProData_i$ by the following formula:

$$\begin{cases} CorrFac = \dfrac{\text{Max}(TestSetLabel_i) - \text{Min}(TestSetLabel_i)}{\text{Max}(ProData_i) - \text{Min}(ProData_i)}, i = 0, \ldots, n-1 \\ CorrData_i = (ProData_i - 0.5) \times CorrFac + 0.5 \end{cases}$$

Wherein, CorrFac represents the boundary correction factor, Max( ) represents the maximum value, i represents the serial number, $TestSetLabel_i$ represents the $i^{th}$ test set tag value, Min( ) represents finding the minimum value, $ProData_i$ represents the $i^{th}$ data after sliding window correction, and n represents the maximum value of i, and $CorrData_i$ represents the final result value after boundary correction.

After boundary correction, compared with before the processing, its range ability is basically consistent with the source data, and the predicted value is closer to the true value. The final model selected in this disclosure is a hybrid model of Regression LSTM corrected by a voting algorithm with a sliding window sized 21. After verification set testing, its $R^2$ score is 0.8992 and the predicted time is 1095.4372 ms.

Figure 3:
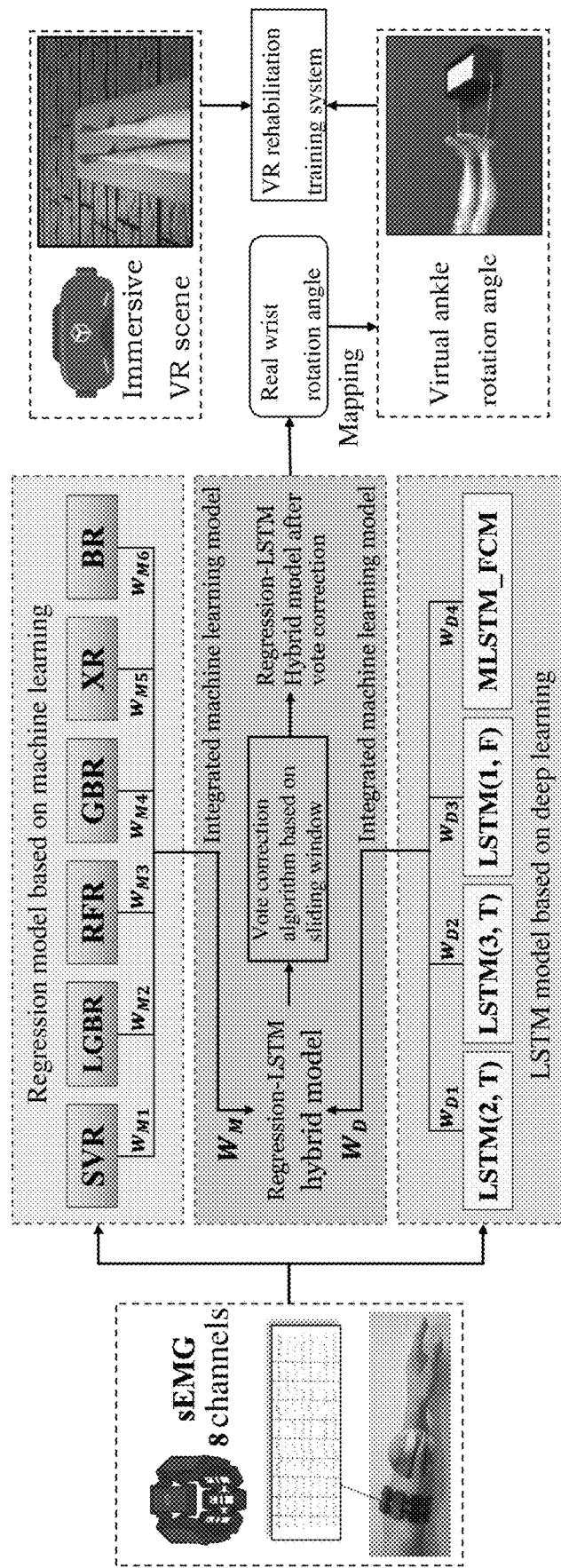
FIG. 3 is a schematic diagram of a hybrid network model Regression LSTM connection and data flow of an immersive ankle rehabilitation training method based on upper limb motion signals according to this disclosure.

FIG. 3 shows the connection of various machine learning models and deep learning models in the entire system, and displays the flow of data in the form of arrows. The user drives the real wrist joint to continuously perform continuous wrist dorsiflexion and wrist palm flexion movements. The Myo EMG bracelet collects sEMG signals from 8 channels of the forearm and inputs the EMG data into the machine learning based regression model MLModels and the deep learning based LSTM model DLModels, respectively. The two modules are integrated internally through corresponding weight assignments to obtain the integrated machine learning model MLResult and the integrated deep learning DLResult results. In order to further improve the robustness of the system, different weights are assigned to the obtained two results for further integration, forming a hybrid model based on data-driven Regression LSTM. Due to the weak and easily interfering nature of sEMG signals, the initially obtained sEMG signals may have tremors. Therefore, it is necessary to correct the identified results using a sliding window based voting correction algorithm to obtain the final result RL-VCA (Regression LSTM Hybrid Model Voting-based Correction Algorithm).

The predicted result finally obtained is also a floating point result value of continuous rotation of the real wrist joint. The system then maps this result to the ankle of the avatar in the virtual scene for virtual and real collaborative rotation actions. During this period, users need to wear HTC Vive headsets to personally feel the immersive VR experience.

5. Rehabilitation Training Based on VR Scenes

The ultimate goal of the technology of this disclosure is to target early acute and subacute hemiplegia patients. Due to the incomplete recovery of their active motor function, the rehabilitation therapeutic options available in the early stage are strictly limited, and they cannot rely solely on common instruments or VR systems to complete autonomous rehabilitation training. To this end, an innovative design was made to map the continuous movements of the real wrist joint to the ankle rotation process of the character in a virtual VR scene. During this process, patients were required to constantly observe actions and imagine movements in their minds, until a progressive rehabilitation therapeutic process of imitation learning emerged, awakening the patient's blurred motor memory, which helps the sensory motor center to generate new perception of the limbs, thereby helping patients repair the motor function of damaged neurons.

The entire system scene is built based on the Unity3D game engine (version number 2021.1.18f1). The virtual avatars in the scene are modeled using 3ds MAX, and the system is mainly developed using C # and Python languages. The integrated development environment is Visual Studio 2022 and PyCharm 2022, using Git 2.23.0 for version control and hosting on Github. The program runs on Windows 10.

The hardware equipment of the system mainly consists of a laptop computer for debugging demonstration programs (configured as: Intel Core i7-11800H, 2.3 GHz CPU, 16 GB RAM, NVIDIA Geforce GTX 3070 graphics card), a Myo EMG bracelet for collecting sEMG signals, and an HTC Vive headwear display for providing an immersive experience.

Figure 4:
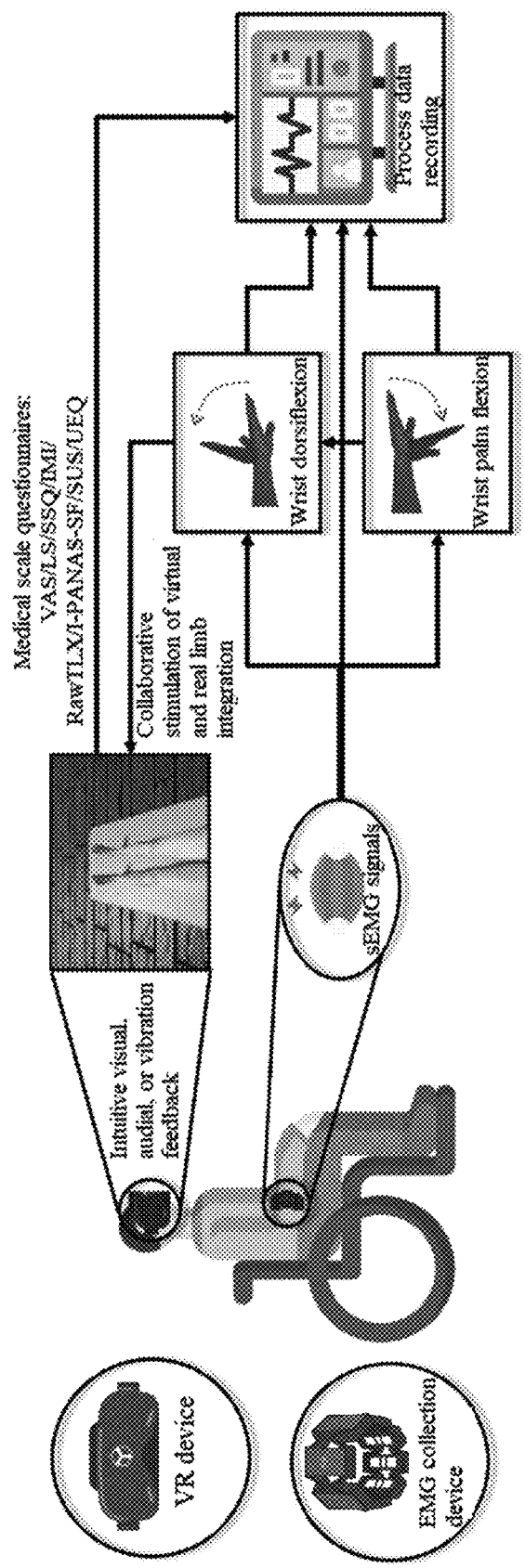
FIG. 4 is an operational schematic diagram of some embodiments of an immersive ankle rehabilitation training method based on upper limb motion signals according to this disclosure.

The overall operational overview of the system is shown in FIG. 4. The user sits upright in a chair, wearing an HTC Vive headwear display and a Myo EMG bracelet. The user continuously makes wrist dorsiflexion or wrist palm flexion movements according to his or her actual condition of illness. The system obtains the forearm sEMG signal in real-time, and predicts the current wrist joint change angle based on the hybrid model of Regression LSTM corrected by the sliding window based voting algorithm in Chapter 3, then maps it to the ankle of the character in the virtual scene for rotation, to achieve collaborative stimulation of virtual and real limb integration. The user's HTC Vive head display will provide corresponding feedback with intuitive visual, audial, and Myo EMG bracelet vibrations. After completing rehabilitation training, users need to fill out the Visual Analog Scale (VAS), Likert Scale (LS), Simulator Sickness Questionnaire (SSQ), Intrinsic Motivation Inventory (IMI), Task Load Index (RawTLX), Positive And Negative Affect Scale (I-PANAS-SF), System Usability Scale (SUS), and User Experience Questionnaire (UEQ) based on their true feelings during the experiment.

This disclosure designs two different rehabilitation training mode scenes for patients with dorsiflexion and plantar flexion. In each scene, there is a virtual avatar with both feet flat and sitting vertically on a yoga mat, with a floor texture added to the ground and a marble texture in front. During testing, the user needs to wear an HTC Vive headwear display and a Myo bracelet to observe the virtual avatar's viewing scene from a first person perspective. The wrist continuously performs wrist dorsiflexion/palm flexion actions, and the system will collect sEMG signal changes from the user's forearm, mapping the continuous actions to the avatar's ankle in the virtual scene to perform foot dorsiflexion/plantar flexion actions with the same rotational amplitude. By constantly repeating this interactive stimulation of virtual and real perception, users can change the degree of contraction and relaxation of their related muscle groups, regulate subjective consciousness, and greatly enhance the users' motor imagination vividness, kinesthetic illusion, and sense of physical belonging, thus achieving the goal of rehabilitation.

Figure 5:
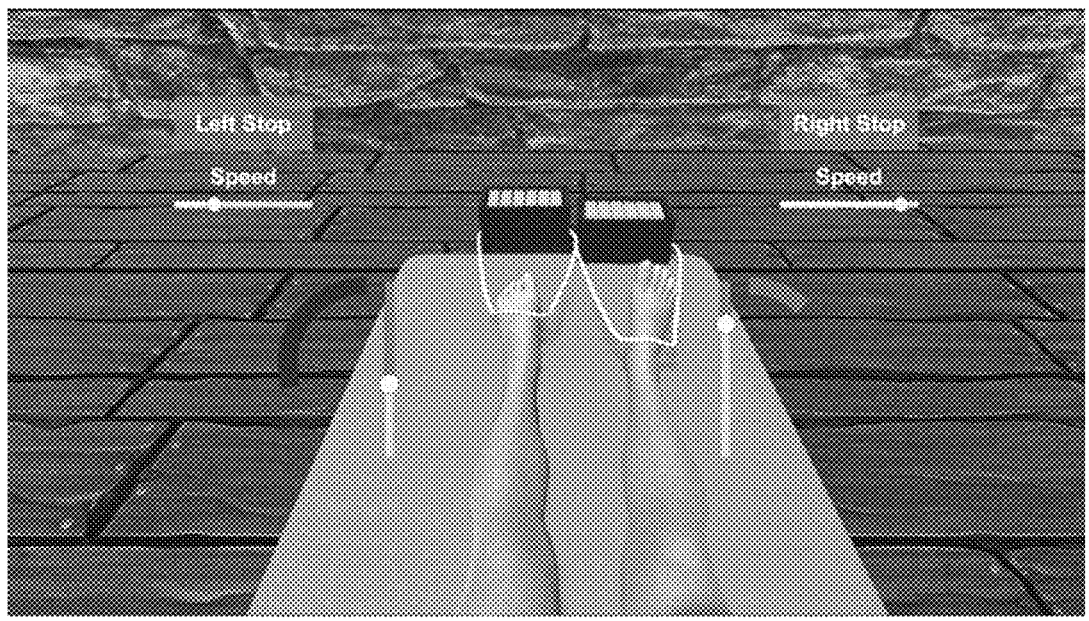
FIG. 5 is a foot dorsiflexion rehabilitation scene for the VR training system of an immersive ankle rehabilitation training method based on upper limb motion signals according to this disclosure.

FIG. 5 shows the rehabilitation training scene for foot dorsiflexion, mainly designed for patients whose ankles cannot complete dorsiflexion. This scene is a treasure box pulling game where two treasure boxes filled with gold bars are tied to the virtual avatar's feet by ropes. During the actual operation, users need to perform corresponding wrist dorsiflexion actions to pull the treasure boxes towards themselves as much as possible. Afterwards, the treasure boxes are reset and the previous process is repeated. During the entire process of performing the action, patients try to imagine in their minds that they are controlling their real ankles to pull the treasure boxes. By continuously repeating this process of imagination, the patients' previously damaged ankle dorsiflexion motor neurons may be repaired.

Figure 6:
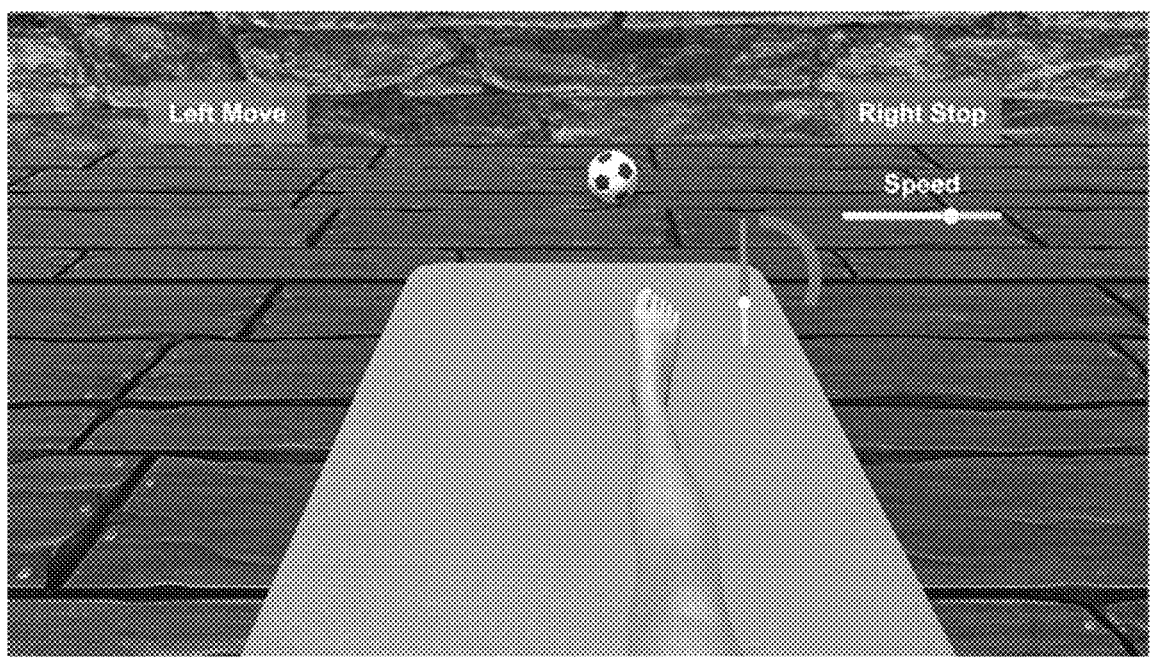
FIG. 6 is a foot plantar flexion rehabilitation scene for the VR training system of an immersive ankle rehabilitation training method based on upper limb motion signals according to this disclosure.

FIG. 6 shows the rehabilitation training scene for plantar flexion of foot, mainly designed for patients whose ankles cannot complete plantar flexion. This scene is a football pushing game where a football is placed directly in front of the virtual avatar's foot. In actual operation, users need to perform corresponding wrist palm flexion action, then the predicted results will be mapped to the virtual ankle in the VR scene for foot plantar flexion action, pushing the ball forward, and when the ball touches the granite wall, it will rebound towards the user's direction, the user at the time needs to continue performing wrist and palm flexion actions after the football rebounds back. Repeat this process continuously. During the entire exercise process, patients try their best to imagine in their minds that they are controlling the real ankle to push the football. By continuously repeating this process of imagination, the damaged ankle plantar flexor motor neurons may be repaired.

There are buttons in the upper left and upper right of the two scenes to control whether the legs are to be displayed, mainly for upper and lower limb alignment and direction coordination training (such as upper left and lower right limbs). This method is more conducive to improving motor ability and brain fitness training. To display the leg on the current side, click on the "Left Move" or the "Right Move" button, the prompt on the button at the time will change to "Left Stop" or "Right Stop", and the virtual leg, rate control bar, and horizontal and vertical scrolling progress bars in two different dimensional directions will appear simultaneously, wherein, the rate control bar Speed is used to control the rate of change of the scrolling progress bar, and can be adjusted by a rehabilitation therapist, the scrolling progress bar continuously changes at a constant speed in both horizontal and vertical directions, with the main purpose of providing users with a reference rate of wrist dorsiflexion and wrist palm flexion movements, so that they can follow the wrist joint movement.

Figure 7:
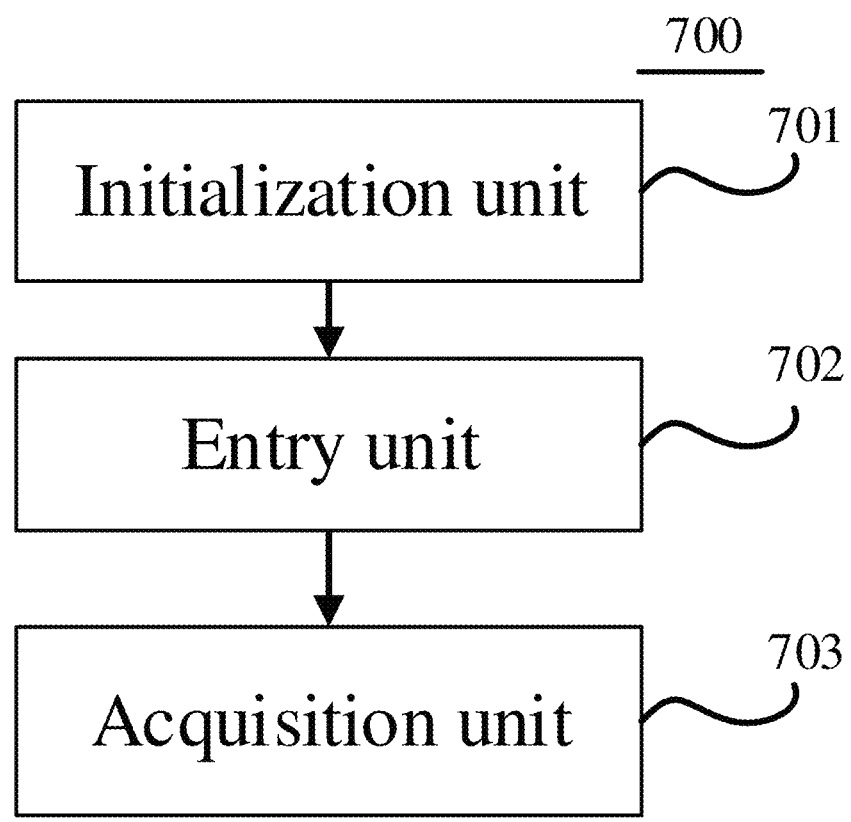
FIG. 7 is a structural schematic diagram of some embodiments of an immersive ankle rehabilitation training method based on upper limb motion signals according to this disclosure.

Further referring to FIG. 7, as an implementation of the methods shown in the above figures, this disclosure provides some embodiments of an immersive ankle rehabilitation training device based on upper limb motion signals. These device embodiments correspond to method embodiments, and the immersive ankle rehabilitation training device based on upper limb motion signals can be specifically applied to various electronic apparatuses.

As shown in FIG. 7, an immersive ankle rehabilitation training device 700 based on upper limb motion signals comprises: an initialization unit 701, an entry unit 702, and an acquisition unit 703, wherein, the initialization unit 701 is configured to initialize a hybrid network model, Regression LSTM model, and in combination with a filtering vote correction algorithm based on a sliding window, to perform recognition of sEMG signals; the entry unit 702 is configured to enter a virtual and real collaborative interactive feedback rehabilitation training system based on continuous sEMG signals, wherein the training system comprises two virtual training scenes, namely a treasure box pulling virtual training scene for foot dorsiflexion training and a football pushing virtual training scene for foot plantar flexion training; the acquisition unit 703 is configured to collect 8 channels of forearm sEMG signals through an EMG bracelet to monitor hand movement, and control the contralateral virtual lower limb displayed on the VR headwear display for rehabilitation training, wherein the EMG monitoring bracelet is worn on the user's forearm, the VR headwear display is worn on the user's head, and the user sits upright in a chair.

It should be understood that the various units in the immersive ankle rehabilitation training device based on upper limb motion signals correspond to the various steps in the method. Therefore, the operations, features, and beneficial effects described above for the method are also applicable to the immersive ankle rehabilitation training device based on upper limb motion signals and the units included therein, and will not be further elaborated here.

Figure 8:
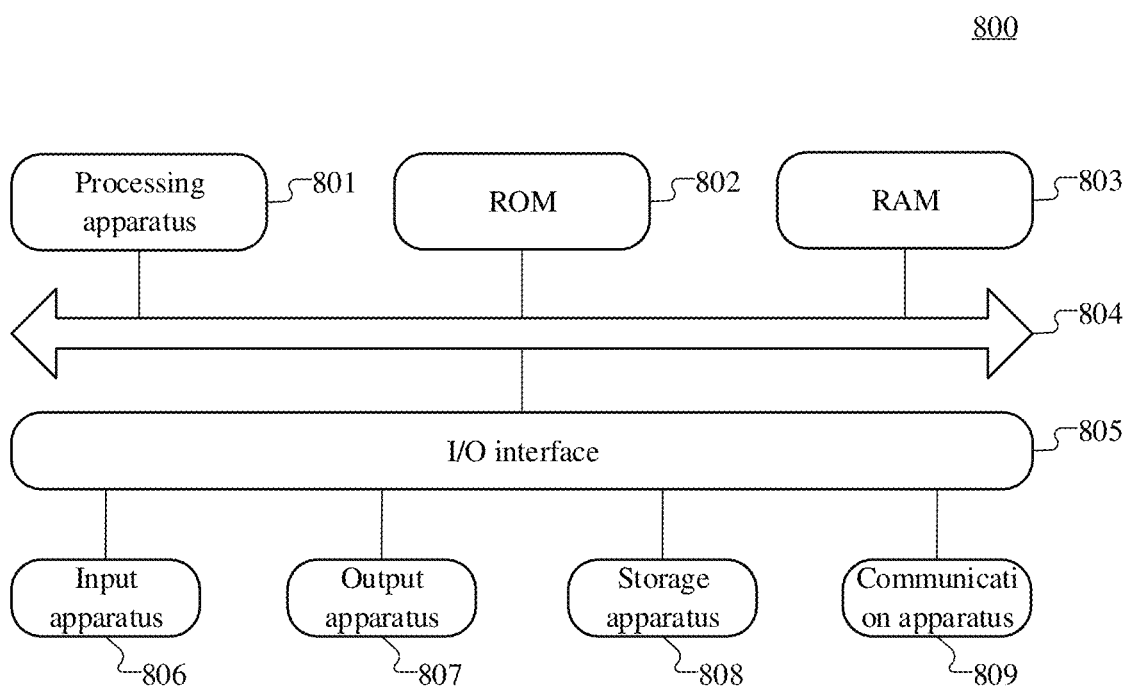
FIG. 8 is a schematic diagram of the structure of an electronic apparatus suitable for implementing some embodiments of this disclosure.

Referring to FIG. 8 below, a structural schematic diagram of an electronic apparatus (such as an electronic apparatus) 800 suitable for implementing some embodiments of this disclosure is shown. The electronic apparatus shown in FIG. 8 is only an example and should not impose any limitations on the functionality and scope of use of the embodiments of this disclosure.

As shown in FIG. 8, electronic apparatus 800 may comprise a processing device (such as a central processing unit, graphics processor, etc.) 801, which may perform various appropriate actions and processes based on programs stored in read-only memory (ROM) 802 or programs loaded from storage device 808 into random access memory (RAM) 803. In RAM 803, various programs and data required for the operation of electronic apparatus 800 are also stored. The processing device 801, ROM 802, and RAM 803 are connected to each other through bus 804. Input/output (I/O) interface 805 is also connected to bus 804.

Typically, the following devices can be connected to I/O interface 805: input devices 806, such as touch screens, touchpads, keyboards, mice, cameras, microphones, accelerometers, gyroscopes, etc.; output devices 807, such as liquid crystal displays (LCDs), speakers, vibrators, etc.; storage devices 808, such as magnetic tapes, hard drives, etc.; and communication device 809. The communication device 809 may allow electronic apparatus 800 to communicate wirelessly or wirelessly with other apparatuses to exchange data. Although FIG. 8 illustrates electronic apparatus 800 with various devices, it should be understood that it is not required to implement or possess all the illustrated devices, but may implement alternatively or have more or fewer devices. Each box shown in FIG. 8 may represent one device or multiple devices as needed.

Specifically, according to some embodiments of this disclosure, the process described above with reference to the flowchart may be implemented as a computer software program. For example, some embodiments of this disclosure include a computer program product that comprises a computer program hosted on a computer-readable medium, the computer program comprises program code for executing the method shown in the flowchart. In some of such embodiments, the computer program may be downloaded and installed from the network through communication device 809, or installed from storage device 808, or installed from ROM 802. When the computer program is executed by processing device 801, the above-mentioned functions defined in some embodiments of this disclosure are executed.

It should be noted that, the above computer readable medium in some embodiments of this disclosure may be a computer readable signal medium, a computer readable storage medium, or any combination of the two. Computer readable storage media may be, for example, but not limited to, systems, devices or components of electricity, magnetism, light, electromagnetism, infrared, or semiconductors, or any combination of the above. More specific examples of computer readable storage media may include, but are not limited to: electrical connections with one or more wires, portable computer disks, hard drives, random access memory (RAM), read-only memory (ROM), erasable programmable read-only memory (EPROM or flash memory), optical fibers, portable compact disk read-only memory (CD-ROM), optical storage devices, magnetic storage devices, or any suitable combination of the above. In some embodiments of this disclosure, computer readable storage media may be any tangible media containing or storing a program, which can be used by or in combination with an instruction execution system, device, or component. In some embodiments of this disclosure, computer readable signal media may include data signals propagated in the baseband or as part of the carrier, which carry computer readable program codes. This propagation of data signals may take various forms, comprising but not limited to electromagnetic signals, optical signals, or any suitable combination of the above. Computer readable signal media may also be any computer readable media other than computer readable storage media, which can send, propagate, or transmit programs for use by or in combination with an instruction execution system, device, or component. The program codes contained on computer readable media may be transmitted using any suitable media, comprising but not limited to: wires, optical cables, RF (radio frequency), etc., or any suitable combination of the above.

In some implementations, clients and servers may communicate using any currently known or future developed network protocols such as HTTP (Hyper Text Transfer Protocol), and may interconnect with any form or medium of digital data communication (such as communication networks). Examples of communication networks include local area networks (LANs), wide area networks (WANs), internets (such as the Internet), and end-to-end networks (such as ad hoc end-to-end networks), as well as any currently known or future developed networks.

The computer readable media mentioned above may be included in the electronic apparatus mentioned above, or exist separately without being assembled into the electronic apparatus. The computer readable media mentioned above carry one or more programs, and when the one or more of programs are executed by the electronic apparatus, the electronic apparatus is made to: Step 1, initialize a hybrid network model, Regression LSTM model, and in combination with a filtering vote correction algorithm based on a sliding window, to perform recognition of sEMG signals; Step 2, enter a virtual and real collaborative interactive feedback rehabilitation training system based on continuous sEMG signals, wherein the training system comprises two virtual training scenes, namely a treasure box pulling virtual training scene for foot dorsiflexion training and a football pushing virtual training scene for foot plantar flexion training; Step 3: collect 8 channels of forearm sEMG signals through an EMG bracelet to monitor hand movement, and control the contralateral virtual lower limb displayed on the VR headwear display for rehabilitation training, wherein the EMG monitoring bracelet is worn on the user's forearm, the VR headwear display is worn on the user's head, and the user sits upright in a chair.

The computer program codes for executing some embodiments of this disclosure may be written in one or more programming languages or combinations thereof, the programming languages comprising object-oriented programming languages such as Java, Smalltalk, C++, and conventional procedural programming languages such as "C" or similar programming languages. Program codes may be completely executed on the user's computer, partially executed on the user's computer, executed as a standalone software package, partially executed on the user's computer and partially executed on a remote computer, or completely executed on a remote computer or server. In cases involving a remote computer, the remote computer may be connected to the user's computer through any type of network, comprising a local area network (LAN) or wide area network (WAN), or may be connected to an external computer (such as using an Internet service provider to connect through the Internet).

The flowcharts and block diagrams in the accompanying drawings illustrate the possible architecture, functions, and operations of systems, methods, and computer program products according to various embodiments of this disclosure. At this point, each box in a flowchart or block diagram may represent a module, program segment, or part of code that contains one or more executable instructions for implementing specified logical functions. It should also be noted that in some alternative implementations, the functions indicated in the boxes may also occur in a different order than those indicated in the drawings. For example, two consecutive boxes may actually be executed in parallel, and sometimes they may also be executed in reverse order, depending on the functions involved. It should also be noted that each box in the block diagram and/or flowchart, as well as the combination of boxes in the block diagram and/or flowchart, may be implemented using dedicated hardware based systems that perform specified functions or operations, or may be implemented using a combination of dedicated hardware and computer instructions.

The units described in some embodiments of this disclosure may be implemented through software or hardware. The described units may also be set in a processor, for example, it may be described as: a processor comprising an initialization unit, an entry unit, and an acquisition unit. Wherein, the names of these units do not constitute limitations to the units per se in some cases. For example, the determining unit may also be described as a "unit that initializes the hybrid network model Regression LSTM model and in combination with a filtering vote correction algorithm based on a sliding window to recognize sEMG signals".

The functions described above in this article may be at least partially executed by one or more hardware logic components. For example, unrestrictedly, exemplary hardware logic components may be used, comprising: Field Programmable Gate Arrays (FPGAs), Application Specific Integrated Circuits (ASICs), Application Specific Standard Products (ASSPs), System On Chip (SOC), Complex Programmable Logic Devices (CPLDs), and so on.

The above description is merely some preferred embodiments of this disclosure and illustrations of the applied technical principles. Those skilled in the art should understand that the scope of the disclosure involved in the embodiments of this disclosure is not limited to the technical solutions formed by the specific combination of the above technical features, and should cover at the same time, without departing from the above inventive concept, other technical solutions formed by any combination of the above technical features or their equivalent features, for example, a technical solution formed by replacing the above features with the technical features of similar functions disclosed (but not limited to) in the embodiments of this disclosure.

The invention claimed is:

1. An immersive ankle rehabilitation training method based on upper limb motion signals, comprising:
   step 1, initializing a hybrid network model, Regression LSTM model, and in combination with a filtering vote correction algorithm based on a sliding window, to perform recognition of surface electromyography (sEMG) signals;
   step 2, entering a virtual and real collaborative interactive feedback rehabilitation training system based on continuous sEMG signals, wherein, the training system comprises two virtual training scenes, namely a treasure box pulling virtual training scene for foot dorsiflexion training and a football pushing virtual training scene for foot plantar flexion training; and
   step 3, collecting 8 channels of forearm sEMG signals through an EMG bracelet to monitor hand movement, and controlling contralateral virtual lower limb displayed on a VR headwear display for rehabilitation training, wherein, the EMG monitoring bracelet is worn on a user's forearm, the VR headwear display is worn on the user's head, and the user sits upright in a chair.

2. The method of claim 1, wherein the Regression LSTM model is obtained by weighting a machine learning based regression model Regression and a deep learning based long and short term memory network LSTM, and the weighting is based on a determination coefficient R2 score of a training sample.

3. The method of claim 2, wherein the filtering vote correction algorithm based on a sliding window comprises:
   introducing a sliding window, wherein, a number of small windows selected by the sliding window is odd so as to calculate symmetry, and each small window is assigned a weight value;
   filling an entire sliding window up with an odd number of original sEMG signal values;
   starting from half the sliding window, calculating this value by multiplying a weight of the entire sliding window by the odd number of original sEMG signal values to obtain a correction value, with a calculation formula as follows:

$$ProData_i = \sum_{j=-\lfloor \frac{w}{2} \rfloor}^{\lfloor \frac{w+1}{2} \rfloor} W_{j+\lfloor \frac{w}{2} \rfloor} \times RawData_{i+j},$$

wherein, i represents a serial number, ProData$_i$ represents a ith data after sliding window correction, Σ represents a summation symbol, w represents a size of the sliding window, j represents a serial number, W represents a weight value of the sliding window, and represents the weight value of the $j^{th}$ sliding window, RawData$_{i+j}$ represents a (i+j) th data among the odd number of original sEMG signal values; and
based on the sliding window voting correction algorithm, iterative calculation is carried out sequentially until a $$(n - \lfloor \frac{w}{2} \rfloor)^{th}$$

data, then the $$\lfloor \frac{w}{2} + 1 \rfloor^{th}$$

original sEMG signal values are filled in, wherein n represents a maximum value of i, and compared to existing sliding window algorithms, an additional original sEMG signal value is filled in to overlay adjacent windows to ensure a smooth transition of sEMG continuous signals;
performing boundary correction on the processed data ProData$_i$ using the following formula:

$$\begin{cases} CorrFac = \frac{\text{Max}(TestSetLabel_i) - \text{Min}(TestSetLabel_i)}{\text{Max}(ProData_i) - \text{Min}(ProData_i)}, i = 0, \ldots, n-1 \\ CorrData_i = (ProData_i - 0.5) \times CorrFac + 0.5 \end{cases}$$

wherein, CorrFac represents a boundary correction factor, Max() represents finding a maximum value, i represents the serial number, TestSetLabel$_i$ represents a $i^{th}$ test set label value, Min () represents finding a minimum value, ProData$_i$ represents the $i^{th}$ data after sliding window correction, and n represents the maximum value of i, and CorrData$_i$ represents a final result value after boundary correction.

4. The method of claim 3, wherein, each of two virtual training scenes included in the training system has a virtual avatar, two feet of the virtual avatar are placed flat and vertically on a yoga mat, and a floor texture is added to a ground, front is a marble texture, there are buttons in an upper left and upper right of the two scenes respectively to control whether legs are to be displayed, for upper and lower limb alignment and direction coordination training.

5. The method of claim 4, wherein, the virtual training scene included in the training system has "Left Move" or "Right Move" buttons; if to display a leg on current side, then click on the "Left Move" or the "Right Move" button, a prompt on the button at this time will change to "Left Stop" or "Right Stop", and a virtual leg, rate control bar, and horizontal and vertical scrolling progress bars in two different dimensional directions will appear simultaneously, wherein, the rate control bar is used to control a rate of change of the scrolling progress bars, the scrolling progress bars continuously changes at a constant speed in both horizontal and vertical directions, with a main purpose of providing users with a reference rate of wrist dorsiflexion and wrist palm flexion movements, so that they can follow a wrist joint movement.

6. The method of claim 5, wherein, the controlling contralateral virtual lower limb displayed on the VR headwear display for rehabilitation training comprises:
   using a contralateral wrist sEMG signal of a trained lower limb as a start and control signal for rehabilitation training;
   collecting the sEMG signal changes of the user's forearm, and mapping continuous actions to the character's ankle in the virtual scene to perform the same degree of rotation of the foot dorsiflexion/plantar flexion, wherein, the user needs to wear the VR headwear display and the EMG monitoring bracelet to observe a virtual avatar's view of the scene from a first person perspective, and the contralateral wrist of a virtual foot continuously performs wrist dorsiflexion/palm flexion movements.

7. The method of claim 6, wherein, the method further comprises:
receiving Visual Analog Scale (VAS), Likert Scale (LS), Simulator Sickness Questionnaire (SSQ), Intrinsic Motivation Inventory (IMI), Task Load Index (Raw-TLX), Positive And Negative Affect Scale (I-PANAS-SF), System Usability Scale (SUS), and User Experience Questionnaire (UEQ) filled out by the user after completing rehabilitation training, to assist in evaluating a rehabilitation effect.

8. An electronic apparatus, comprising:
one or more processors;
a storage device, on which are stored one or more programs;
when the one or more programs are executed by the one or more processors, the one or more processors carry out the method stated by claim 1.

9. The electronic apparatus according to claim 8, wherein, the Regression LSTM model is obtained by weighting a machine learning based regression model Regression and a deep learning based long and short term memory network LSTM, and the weighting is based on a determination coefficient $R^2$ score of a training sample.

10. The electronic apparatus according to claim 8, wherein the filtering vote correction algorithm based on a sliding window comprises:
introducing a sliding window, wherein, a number of small windows selected by the sliding window is odd so as to calculate symmetry, and each small window is assigned a weight value;
filling an entire sliding window up with an odd number of original sEMG signal values;
starting from half the sliding window, calculating this value by multiplying a weight of the entire sliding window by the odd number of original sEMG signal values to obtain a correction value, with a calculation formula as follows:

$$ProData_i = \sum_{j=-\lfloor\frac{w}{2}\rfloor}^{\lfloor\frac{w}{2}+1\rfloor} W_{j+\lfloor\frac{w}{2}\rfloor} \times RawData_{i+j},$$

wherein, i represents a serial number, $ProData_i$ represents a $i^{th}$ data after sliding window correction, $\Sigma$ represents a summation symbol, w represents a size of the sliding window, j represents a serial number, W represents a weight value of the sliding window, and represents the weight value of the $j^{th}$ sliding window, $RawData_{i+j}$ represents a (i+j) th data among the odd number of original sEMG signal values; and
based on the sliding window voting correction algorithm, iterative calculation is carried out sequentially until a $$(n-\lfloor\frac{w}{2}\rfloor)^{th}$$

data, then the $$\lfloor\frac{w}{2}+1\rfloor^{th}$$

original sEMG signal values are filled in, wherein n represents a maximum value of i, and compared to existing sliding window algorithms, an additional original sEMG signal value is filled in to overlay adjacent windows to ensure a smooth transition of sEMG continuous signals;
performing boundary correction on the processed data $ProData_i$ using the following formula:

$$\begin{cases} CorrFac = \frac{\text{Max}(TestSetLabel_i) - \text{Min}(TestSetLabel_i)}{\text{Max}(ProData_i) - \text{Min}(ProData_i)}, i = 0, \ldots, n-1 \\ CorrData_i = (ProData_i - 0.5) \times CorrFac + 0.5 \end{cases}$$

wherein, CorrFac represents a boundary correction factor, Max() represents finding a maximum value, i represents the serial number, $TestSetLabel_i$ represents a $i^{th}$ test set label value, Min() represents finding a minimum value, ProData represents the $i^{th}$ data after sliding window correction, and n represents the maximum value of i, and $CorrData_i$ represents a final result value after boundary correction.

11. The electronic apparatus according to claim 8, wherein each of two virtual training scenes included in the training system has a virtual avatar, two feet of the virtual avatar are placed flat and vertically on a yoga mat, and a floor texture is added to a ground, front is a marble texture, there are buttons in an upper left and upper right of the two scenes respectively to control whether legs are to be displayed, for upper and lower limb alignment and direction coordination training.

12. The electronic apparatus according to claim 8, wherein the virtual training scene included in the training system has "Left Move" or "Right Move" buttons; if to display a leg on current side, then click on the "Left Move" or the "Right Move" button, a prompt on the button at this time will change to "Left Stop" or "Right Stop", and a virtual leg, rate control bar, and horizontal and vertical scrolling progress bars in two different dimensional directions will appear simultaneously, wherein, the rate control bar is used to control a rate of change of the scrolling progress bars, the scrolling progress bars continuously changes at a constant speed in both horizontal and vertical directions, with a main purpose of providing users with a reference rate of wrist dorsiflexion and wrist palm flexion movements, so that they can follow a wrist joint movement.

13. The electronic apparatus according to claim 8, wherein the controlling contralateral virtual lower limb displayed on the VR headwear display for rehabilitation training comprises:
using a contralateral wrist sEMG signal of a trained lower limb as a start and control signal for rehabilitation training; and
collecting the sEMG signal changes of the user's forearm, and mapping continuous actions to the character's ankle in the virtual scene to perform the same degree of rotation of the foot dorsiflexion/plantar flexion, wherein, the user needs to wear the VR headwear display and the EMG monitoring bracelet to observe a virtual avatar's view of the scene from a first person perspective, and the contralateral wrist of a virtual foot continuously performs wrist dorsiflexion/palm flexion movements.

14. The electronic apparatus according to claim 8, wherein the method further comprises:
receiving Visual Analog Scale (VAS), Likert Scale (LS), Simulator Sickness Questionnaire (SSQ), Intrinsic Motivation Inventory (IMI), Task Load Index (Raw-TLX), Positive And Negative Affect Scale (I-PANAS-SF), System Usability Scale (SUS), and User Experience Questionnaire (UEQ) filled out by the user after completingrehabilitation training, to assist in evaluating a rehabilitation effect.

15. A computer readable medium with computer programs stored thereon, wherein the computer programs, when executed by a processor, carry out the method stated by claim 1.

16. The computer readable medium with computer programs according to claim 15, wherein the Regression LSTM model is obtained by weighting a machine learning based regression model Regression and a deep learning based long and short term memory network LSTM, and the weighting is based on a determination coefficient R2 score of a training sample.

17. The computer readable medium with computer programs according to claim 15, wherein, the filtering vote correction algorithm based on a sliding window comprises:
introducing a sliding window, wherein, a number of small windows selected by the sliding window is odd so as to calculate symmetry, and each small window is assigned a weight value;
filling an entire sliding window up with an odd number of original sEMG signal values;
starting from half the sliding window, calculating this value by multiplying a weight of the entire sliding window by the odd number of original sEMG signal values to obtain a correction value, with a calculation formula as follows:

$$ProData_i = \sum\nolimits_{j=-\lfloor\frac{w}{2}\rfloor}^{\lfloor\frac{w}{2}+1\rfloor} W_{j+\lfloor\frac{w}{2}\rfloor} \times RawData_{i+j},$$

wherein, i represents a serial number, $ProData_i$ represents a $i^{th}$ data after sliding window correction, $\Sigma$ represents a summation symbol, w represents a size of the sliding window, j represents a serial number, W represents a weight value of the sliding window, and represents the weight value of the $j^{th}$ sliding window, $RawData_{i+j}$ represents a (i+j) th data among the odd number of original sEMG signal values; and
based on the sliding window voting correction algorithm, iterative calculation is carried out sequentially until a $$\left(n-\left\lfloor\frac{w}{2}\right\rfloor\right)^{th}$$

data, then the $$\left\lfloor\frac{w}{2}+1\right\rfloor^{th}$$

original sEMG signal values are filled in, wherein n represents a maximum value of i, and compared to existing sliding window algorithms, an additional original sEMG signal value is filled in to overlay adjacent windows to ensure a smooth transition of sEMG continuous signals;
performing boundary correction on the processed data $ProData_i$ using the following formula:

$$\begin{cases} CorrFac = \dfrac{\text{Max}(TestSetLabel_i) - \text{Min}(TestSetLabel_i)}{\text{Max}(ProData_i) - \text{Min}(ProData_i)}, i=0, \dots, n-1 \\ CorrData_i = (ProData_i - 0.5) \times CorrFac + 0.5 \end{cases}$$

wherein, CorrFac represents a boundary correction factor, Max() represents finding a maximum value, i represents the serial number, $TestSetLabel_i$ represents a $i_{th}$ test set label value, Min() represents finding a minimum value, $ProData_i$ represents the ith data after sliding window correction, and n represents the maximum value of i, and $CorrData_i$ represents a final result value after boundary correction.

18. The computer readable medium with computer programs according to claim 15, wherein each of two virtual training scenes included in the training system has a virtual avatar, two feet of the virtual avatar are placed flat and vertically on a yoga mat, and a floor texture is added to a ground, front is a marble texture, there are buttons in an upper left and upper right of the two scenes respectively to control whether legs are to be displayed, for upper and lower limb alignment and direction coordination training.

19. The computer readable medium with computer programs according to claim 15, wherein the virtual training scene included in the training system has "Left Move" or "Right Move" buttons; if to display a leg on current side, then click on the "Left Move" or the "Right Move" button, a prompt on the button at this time will change to "Left Stop" or "Right Stop", and a virtual leg, rate control bar, and horizontal and vertical scrolling progress bars in two different dimensional directions will appear simultaneously, wherein, the rate control bar is used to control a rate of change of the scrolling progress bars, the scrolling progress bars continuously changes at a constant speed in both horizontal and vertical directions, with a main purpose of providing users with a reference rate of wrist dorsiflexion and wrist palm flexion movements, so that they can follow a wrist joint movement.

20. An immersive ankle rehabilitation training device based on upper limb motion signals, comprising:
an initialization unit, which is configured to initialize a hybrid network model, Regression LSTM model, and in combination with a filtering vote correction algorithm based on a sliding window, to perform recognition of surface electromyography (sEMG) signals;
an entry unit, which is configured to enter a virtual and real collaborative interactive feedback rehabilitation training system based on continuous sEMG signals, wherein, the training system comprises two virtual training scenes, namely a treasure box pulling virtual training scene for foot dorsiflexion training and a football pushing virtual training scene for foot plantar flexion training; and
an acquisition unit, which is configured to collect 8 channels of forearm sEMG signals through an EMG bracelet to monitor hand movement, and control contralateral virtual lower limb displayed on a VR headwear display for rehabilitation training, wherein, the EMG monitoring bracelet is worn on a user's forearm, the VR headwear display is worn on the user's head, and the user sits upright in a chair.

* * * * *